(12) United States Patent
Jakubowicz et al.

(10) Patent No.: US 8,076,126 B2
(45) Date of Patent: Dec. 13, 2011

(54) SINGLE COLUMN IMMUNOLOGICAL TEST ELEMENTS

(75) Inventors: Raymond F. Jakubowicz, Rush, NY (US); Mark Sawczuk, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 524 days.

(21) Appl. No.: 12/175,590

(22) Filed: Jul. 18, 2008

(65) Prior Publication Data

US 2010/0015726 A1   Jan. 21, 2010

(51) Int. Cl.
  *C12M 1/34* (2006.01)
(52) U.S. Cl. ............ 435/287.2; 422/430; 436/541; 436/809
(58) Field of Classification Search .............. None
  See application file for complete search history.

(56) References Cited

U.S. PATENT DOCUMENTS

| | | | |
|---|---|---|---|
| 3,492,396 A * | 1/1970 | Dalton et al. ............ 435/7.25 |
| 4,341,635 A | 7/1982 | Golias |
| 5,512,432 A | 4/1996 | LaPierre et al. |
| 5,512,436 A | 4/1996 | Stone |
| 5,552,064 A | 9/1996 | Chachowski |
| 5,578,269 A | 11/1996 | Yaremko et al. |
| 5,665,558 A | 9/1997 | Frame et al. |
| 5,780,248 A * | 7/1998 | Milchanoski et al. ....... 435/7.25 |
| 5,830,411 A | 11/1998 | Martinell Gisper-Sauch |
| 5,863,802 A * | 1/1999 | Yves et al. ............ 436/518 |
| 5,885,529 A | 3/1999 | Babson et al. |
| 6,004,020 A | 12/1999 | Bartur |
| 6,114,179 A | 9/2000 | Lapierre et al. |
| 6,162,399 A | 12/2000 | Martinell Gisper-Sauch |
| 6,168,760 B1 | 1/2001 | Horn |
| 6,173,603 B1 | 1/2001 | Horn |
| 6,203,706 B1 | 3/2001 | Schwind et al. |
| 6,517,783 B2 | 2/2003 | Horner et al. |
| 6,761,856 B2 | 7/2004 | Baugh et al. |
| 2004/0141882 A1 | 7/2004 | Mimura et al. |
| 2004/0166551 A1 | 8/2004 | Moulds et al. |
| 2004/0169049 A1 | 9/2004 | Giraud |
| 2007/0003438 A1 | 1/2007 | Kobayashi et al. |

FOREIGN PATENT DOCUMENTS

WO  WO 98/36260  8/1998
WO  WO 2006/021648 A3  3/2006

OTHER PUBLICATIONS

European Search Report for EP Application No. 09251816.6; mailed Nov. 20, 2009; 5 pages.

* cited by examiner

*Primary Examiner* — Chris L Chin
(74) *Attorney, Agent, or Firm* — Hiscock & Barclay, LLP

(57) ABSTRACT

A plurality of individual single column test elements are provided for use in a clinical testing apparatus. Each test element is defined by a single test column that includes a quantity of a test material, such as gel material or a bead matrix, including a cover strip used to access the contents of the test column. Individual test elements can be stored, retained and dispensed for testing patient samples.

7 Claims, 4 Drawing Sheets

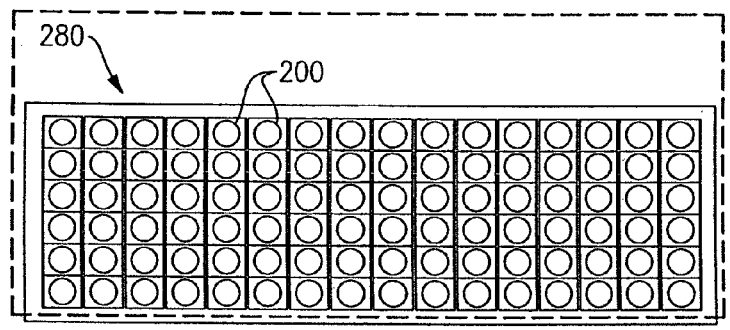
FIG.7
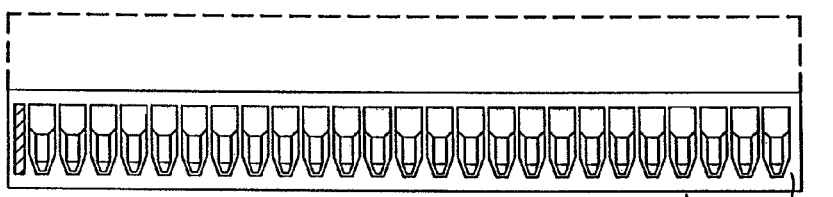
FIG.8
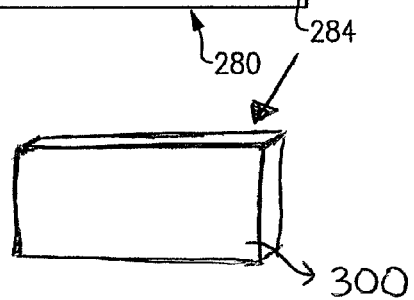

SINGLE COLUMN IMMUNOLOGICAL TEST ELEMENTS

FIELD OF THE INVENTION

This invention relates to the field of immunodiagnostic testing and more specifically to a test element defined by a single disposable column or reaction well that can be used as a replacement for a multiple fixed column gel card or bead cassette test element. Single element columns can be dispensed and used either individually or selectively in groups depending on a specific test or application.

BACKGROUND OF THE INVENTION

Conventionally, it is known to utilize test elements such as gel cards or bead cassettes for blood grouping, antigen or antibody testing, or other related immunohematological applications or uses. These test elements commonly include a planar substrate that supports a plurality of optically transparent and vertically arranged columns or reaction wells. Each of the reaction wells retain a quantity of an inert material, such as glass beads or a gel material, that is mixed within a suspension having an antigen or antibody or is bound therewith. In use in automation, an upper foil layer of at least one card or cassette is pierced or removed, permitting access to the contents of at least one of the reaction wells of the test element for adding patient sample. The sample is then incubated and centrifuged to accelerate an agglutination reaction by means of column agglutination technology (CAT) in which bound red blood cells clump and are filtered by the inert material matrix. The cards or cassettes are usually prearranged and include a fixed and predetermined number of columns to enable a test of interest (e.g., direct or indirect Coombs test, Rh blood typing, ABO blood typing) to be completed.

There may be instances or examples in which all columns of a test card or test cassette may not be necessary in order to conduct a test of interest. However, such test elements, once at least one column thereof is pierced, are often disposed of and not reused, even if available unpierced reaction wells remain in a test element creating unnecessary waste and expense. Moreover, there are a number of situations in which varying the number of test columns is advantageous. Therefore, there is a need to provide versatility as to the types of test elements available, particularly in automated test apparatus.

There is also a general and prevailing need in the field to reduce the overall footprint of automated testing systems, including those systems that employ test elements, such as those that are noted above. To that end, providing any suitable means for reducing or economizing the size of a test element, for storage or otherwise, would be greatly desired.

SUMMARY OF THE INVENTION

According to one version, there is provided a test element for use in an immunodiagnostic test apparatus, said test element comprising a single reaction well having an inert material disposed therein as well as a suspension containing an antigen or antibody or a carrier-bound antigen or antibody and a wrap or seal covering the reaction well. The seal according to one version is selectively pierceable in order to permit access to the contents of the reaction well.

According to another aspect, there is provided a cartridge comprising a frame that retains a plurality of test elements, each said test element comprising a single reaction well having an inert material disposed therein as well as a suspension containing an antigen or antibody or a carrier-bound antibody or antigen as well as a wrap or seal covering the reaction well. The cartridge dispenses the individual test elements for use, whether individually or selectively in any useful number, providing significant versatility and improving overall throughput.

According to another aspect, there is provided an automated testing apparatus comprising a test element supply including a plurality of single column test elements.

Preferably, the automated testing apparatus further includes an incubator and a centrifuge that are each enabled for handling the individual single column test elements whether the test elements are handled individually or within cartridges containing selectively variable numbers of said test elements. As such, the testing apparatus can be configured to operate with a plurality of cartridges between components or modules of the testing apparatus or to provide different assays in conjunction with a test card.

One advantage is a realized reduction in storage capacity volume that can be achieved using the above noted individual test elements in an automated test apparatus, wherein this reduction can be greater than 50 percent.

Another advantage realized is that the individualized test elements pro vide truly random access capability and scheduling in an automated testing apparatus. In addition, throughput enhancement is realized due to reduction in the waiting time for batches.

Yet another advantage realized is cartridge-based packaging of individualized or single column test elements permits easier loading and handling of test elements than found in previously known testing systems.

Still another advantage is that providing individualized test elements insures that there is no reuse of unused columns as in present test elements.

Yet still another advantage provided herein is that the individual test elements enable an extremely small and efficient footprint to be provided in conjunction with test apparatus including those of test element storage, as well as permitting enhanced designs to components and modules used in typical testing apparatus including, for example, centrifuges, incubators, transport assemblies, readers and other components.

The present design is largely facilitated to automated processes and provides better safety as a result. However, the herein described concepts can also be applied to manual based test systems.

These and other features and advantages will become readily apparent from the following Detailed Description, which should be read in conjunction with the accompanying drawings.

BRIEF DESCRIPTION OF THE DRAWINGS

FIG. 7 is a front view of a single element dispensing cartridge in accordance with another embodiment; and FIG. 8 is a top plan view of the dispensing cartridge of FIG. 7.

DETAILED DESCRIPTION

The following discussion relates to a compact consumable test element for patient or other sample testing as well as applications for the single column test element, preferably for use in conjunction with automated test apparatus. It will be apparent to those of sufficient skill from the following description that numerous variations and modifications are possible within the intended scope of the concepts described. In addition, certain terms such as "top", "bottom", "above", "below" and the like are used herein in order to provide a suitable frame of reference with regard to the accompanying drawings. These terms, however, are not intended to be overly limiting, except where so specifically indicated.

Figure 1:
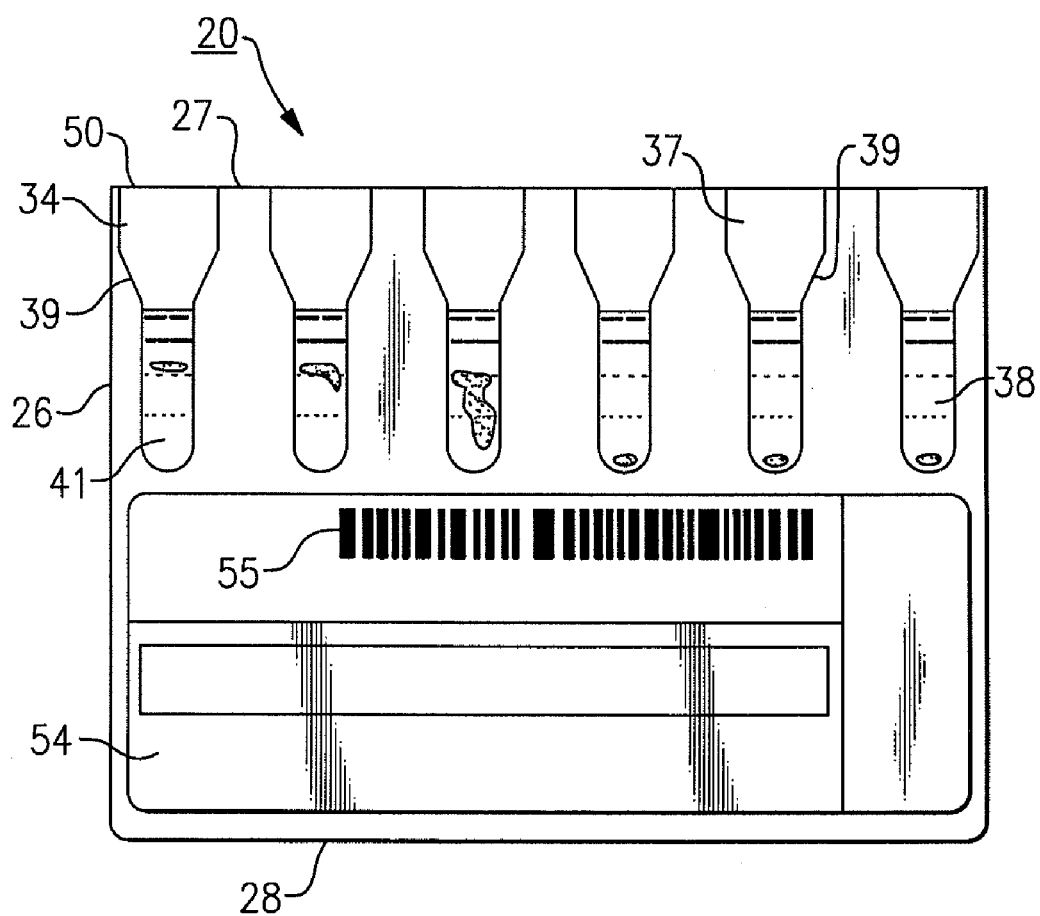
FIG. 1 is a front view of a prior art immunodiagnostic test element.

Referring to FIG. 1, there is shown a prior art test element 20 in the form of a so-called "gel card" or "bead cassette". This element 20 is commonly defined by a planar substrate made from a durable plastic material 26, the substrate having a top side 27 and an opposing bottom side 28. The substrate 26 supports a plurality of optically transparent and vertically arranged test columns or reaction wells 34, each of the reaction wells also being made from a plastic material. In the embodiment shown, a total of six (6) reaction wells 34 are integrally formed within the substrate 26. Each of the reaction wells 34 are further defined by an upper portion 37 having an inner diameter that is significantly larger than that of a lower portion 41. A transitional portion 39 having an inwardly tapering diameter interconnects the upper and lower portions 37, 41. A quantity of an inert material (not shown), such as glass beads or gel material, is provided preferably by the manufacturer within the lower portion 41 of each column, this material being mixed with an antigen or antibody or a carrier-bound antibody or antigen typically in an aqueous suspension or medium. A seal or wrap 50 is attached, such as a pierceable foil, covering the top side 27 of the test element 20 that, when pierced or removed, selectively permits access to the contents of the reaction wells 34. The test element 20 further includes a label 54 located beneath the reaction wells 34 on a front facing side thereof, the label including a bar-coded portion 55, the label and bar-coded portion each including items such as lot number, test type, expiration date, place of manufacture and other information. Additional details relating to the above test elements 20 can be found in U.S. Pat. No. 5,512,436, the entire contents of which are herein incorporated by reference.

Figure 2:
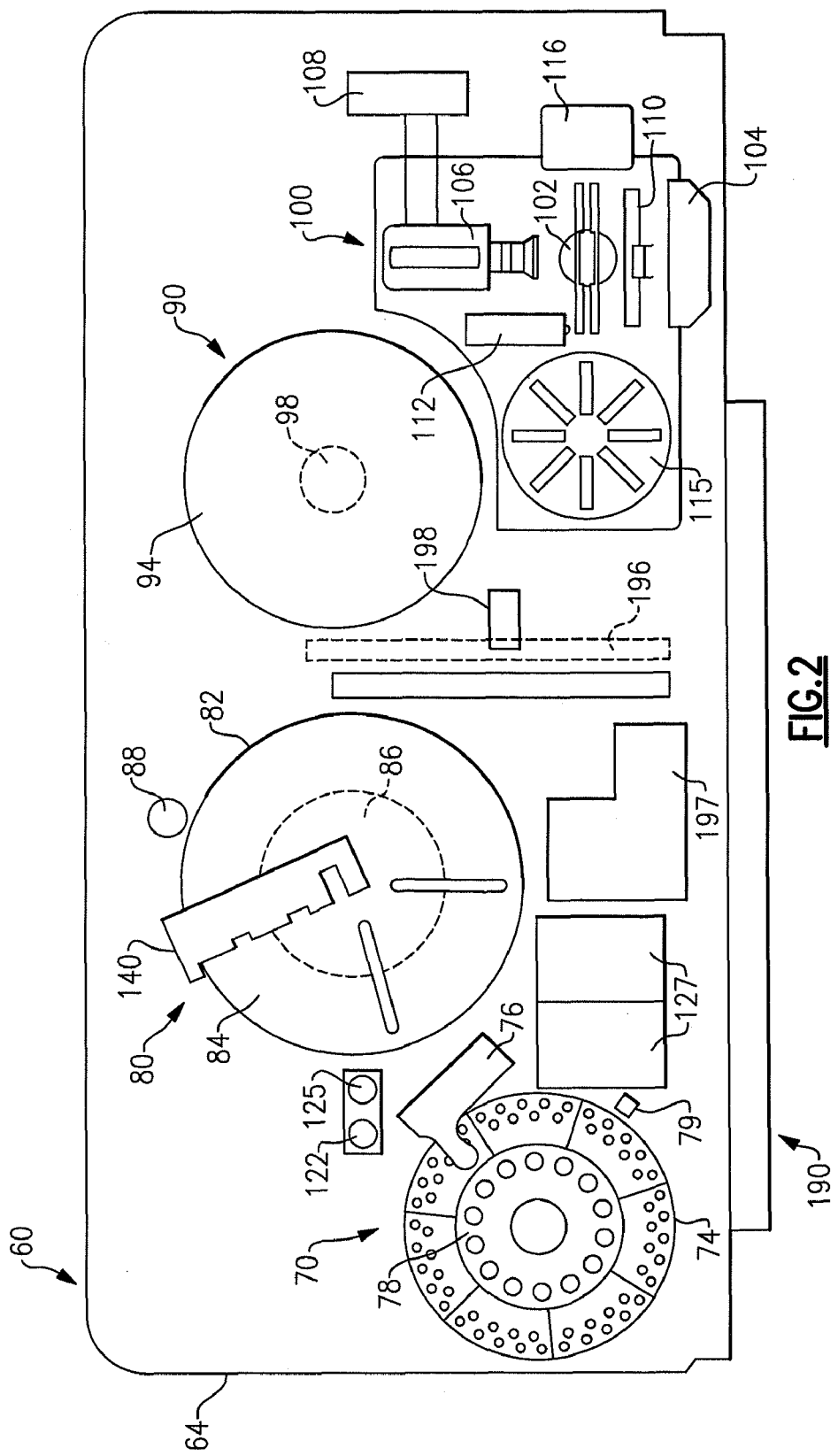
FIG. 2 is a top plan view of a prior art automated test apparatus that utilizes at least test elements, such as those depicted according to FIG. 1.

The herein described immunodiagnostic test element 20 can be used in an automated testing apparatus 60, such as that shown in FIG. 2. In brief and according to this prior art embodiment the testing apparatus 60 includes a frame 64 that retains a number of components including a reagent and sample supply 70, an incubator station 80, a centrifuge 90, an analysis station 100, and a drawer assembly 190. More particularly, the sample and reagent supply 70 of this specific apparatus 60 includes a sample rack 74 as well as a reagent rack 78, each of which contain bottles or vials of patient sample and reagent, respectively. The reagent and sample supply 70 is constructed as a rotor that is rotatable about a center axis by means of a drive mechanism that includes a motor (not shown in this view), wherein a bar code reader 79 is further provided in relation to the reagent and sample supply 70 as well as a tube hold-down assembly 76 disposed over a portion thereof.

The incubator station 80 includes a cassette rack 82 that further includes respective first and second sections 84, 86, as well as a drive mechanism including a motor 88 that selectively rotates each of the sections about a center axis. The centrifuge 90 is known to those in the field and includes a rotor 94 and a motor 98 enabling reactant contained within supported cards to be spun down by centrifugation. The analysis station 100 includes holding means 102, illumination means 104, an imaging subsystem 106, a processing subsystem 108, a transport subsystem 110, a storage rack 115, a bar code reader 112, and a waste receptacle 116. The drawer assembly 190 includes a drawer (not shown), a slide tray (not shown), a motor (not shown), a sensor bar 196, a bar code reader 198 and a holding area 197. A transport assembly (not shown) of the testing apparatus 60 includes a robot arm and a gripper. Finally, a pipette assembly includes a gantry-type pipette that is attached to a robot arm 128, this assembly further including shallow and deep wash areas 122, 125, as well as cell dilution packs 127.

In the testing apparatus 60 shown, for example, a plurality of test elements 20, such as those previously described according to FIG. 1, are initially supported within the drawer and are read by the bar code reader 198. Assuming the read of the test element 20 is successful, the test elements 20 are loaded by means of the transport assembly (not shown) and the gripper into the cassette rack 82 of the incubator 80. A piercing assembly (not shown) is disposed above the first and second sections 84, 86 of the cassette rack 82 of the incubator station 80 and includes a support subassembly having a slide support (not shown) defined by a plurality of puncture needles that are reciprocably movable, such as by means of solenoids (not shown). The incubator station 80, as driven by the motor 88, is used to incubate patient sample added to each of the test columns 34 from one of the vials of the sample rack 74, the incubator further including the assembly 76 that holds down the sample and reagent vials. The pipette of the pipette assembly is used to aspirate sample from the sample rack 74, while the piercing assembly (not shown) is used to puncture each of the reaction wells 34 of the then-incubated test elements 20. Once the puncturing step has been completed, the pipette 124 can then be used to dispense a predetermined quantity of patient sample (and possibly additional reagents) from the sample and reagent supply 70 into each of the reaction wells 34, FIG. 1, wherein the mixture can be suitably incubated.

Following incubation and in the described testing apparatus 60, the test elements 20 are removed from the incubator station 80 by means of the transport assembly to the centrifuge 90 wherein the test elements are then spun down, thereby accelerating an agglutination reaction as red blood cells are clumped together in the presence of coated reagents. The plurality of beads disposed in each reaction well 34 of the test element 20 includes particles having diameters ranging between about 10 and 100 microns, providing a matrix for the red blood cells, but not the heavier formed agglutinates to pass through by filtering. The resulting reaction can be imaged within the analysis station 100 of the testing apparatus 60 by means of the illumination assembly 104 and imaging subsystem 106, the latter being connected to the processing subsystem 108 having machine vision for grading of the reaction. Additional details concerning the foregoing testing apparatus 60, including its mode of operation, are provided in commonly-assigned U.S. Pat. No. 5,578,269 to Yaremko et al., the entire contents of which are herein incorporated by reference.

To that end, each station of the testing apparatus 60, such as the incubator station 80, centrifuge 90 and analysis station 100, must therefore accommodate the test elements 20 and as a result these stations must each be sized appropriately in order to retain same. In the above test apparatus 60, the individual modules must therefore accommodate the entire test card or element 20, FIG. 1, even if all of the columns of the test element are not actually used or required for testing.

Figure 3:
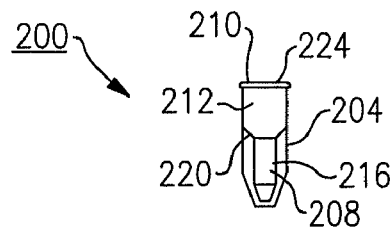
FIG. 3 is a front view of a single column test element in accordance with one embodiment.
Figure 4:
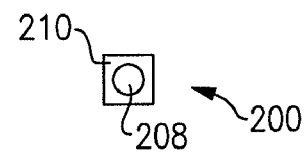
FIG. 4 is a top plan view of the single column test element of FIG. 3.

With the preceding background and referring to FIGS. 3 and 4, there is shown a consumable test element 200 made in accordance with a first embodiment. The test element 200 is defined by a compact body 204 preferably made from a light-weight plastic moldable material that is further defined by a single vertically arranged column or test chamber 208 therein. The column 208 extends downwardly from a top side 210 of the element 200 and is further defined by an upper section 212 having an inner diameter that is significantly larger than that of a lower section 216. An inwardly tapering transitional section 220 is disposed between the upper section 212 and the lower section 216. The test element 200, and more particularly the test column 208, is optically transparent for purposes of detection of reactions occurring therein. A quantity of an inert material (not shown), such as beads or gel material, is added to the lower section 216 of the test column 208 along with a reagent that includes an antigen or antibody or a carrier-bound antigen or antibody formed in an aqueous slurry or medium. A wrap 224 is also added to the top side 210 of the element 200, such as a foil that is adhesively or otherwise attached, to effectively seal the contents of the column 208 in a manner that is commonly known and to protect the contents from contamination. The wrap 224 is preferably and selectively piercable to access the contents of the element 200.

Figure 5:
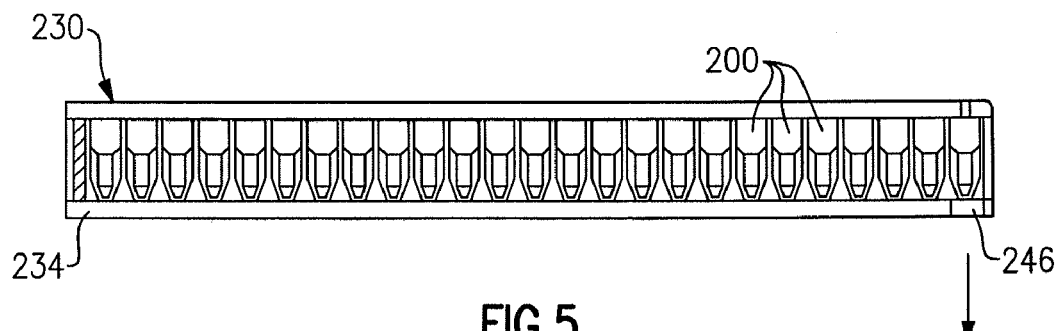
FIG. 5 is a side view of a linear array cartridge of single column test elements of FIGS. 3 and 4.
Figure 6:
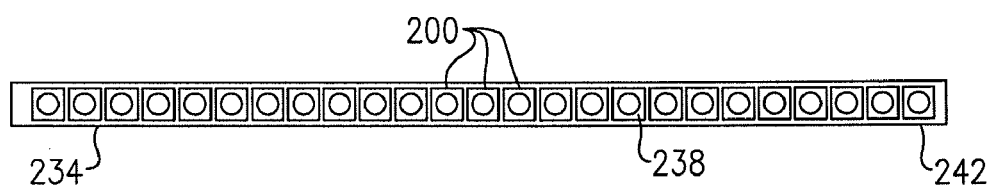
FIG. 6 is a top plan view of the cartridge of FIG. 5.

Referring to FIG. 5 and according to the present embodiment, a plurality (e.g., at least two) of the above-described single column test elements 200 can be individually fitted within a cassette or cartridge 230. The cartridge 230 is defined, according to this embodiment, by a frame 234 having exterior surfaces including a bottom surface and a set of lateral surfaces that are formed in a substantially rectangular configuration, which combine to form an enclosure. The frame 234 according to this embodiment is sized to maintain a predetermined number of test elements 200 in close fitting and adjacent relation with each other in a linear array 238. The number of test elements 200 that are retained as a cartridge can easily be varied depending on the dimensions of the frame 234 that is used. According to this embodiment, the lateral walls of the frame 234 are defined by a height dimension that is essentially equal to that of the test elements 200. In this instance and referring to FIGS. 5 and 6, twenty five (25) test elements 200 are arranged in a one-dimensional linear array 238 for dispensing, such as within an automated testing apparatus (not shown). Moreover, the linear array 238 as shown, permits the test elements 200 to be individually dispensed from an end position 242 of the frame 234 through an appropriately sized slot 246 wherein the cartridge defined herein can function as a test element supply. Therefore and in the array 238 depicted, a test element 200 is ejected vertically through the slot 246, but it will be readily understood by those of adequate skill in the field that the array can assume other configurations such that test elements 200 can be dispensed, for example, horizontally.

In an alternate version, the test elements 200 can also be separately arranged, for example, within a cartridge that like the preceding is defined by a frame sized to permit storage of a plurality of the above described single element test elements. For example, and as shown in FIGS. 7 and 8, a cartridge 280 is defined by a frame 284 that is sized to maintain a two dimensional array of test elements 200 wherein the test elements can be individually dispensed therefrom. In this specific version, ninety six (96) test elements 200 can be retained in close fitting and adjacent relation within the confines of an assemblage having 16 columns and 6 rows totaling 96 test elements, though the specific number of columns and rows can easily be varied depending of the use required and the test apparatus. In this latter version, test elements 200 can actually be repackaged within at least one smaller frame that are sized to retain a specific number of test elements (e.g. 2-8 test elements) depending on the test that is to be performed.

In another version, the test elements can be dispensed from either of the previously described frames into a separate test cartridge 300 that is sized to retain a predetermined number (e.g., greater than two) of test elements 200. As such, the cartridge 300 can be adequately sized to retain any number of test elements wherein the entire cartridge can be loaded and unloaded into modules of the test apparatus (e.g., incubator, centrifuge, etc).

PARTS LIST FOR FIGS. 1-8

20 test element
26 substrate, planar
27 top side
28 bottom side
32 inert material
34 reaction wells or microcolumns
37 upper portion
39 transitional portion
41 lower portion
50 seal or wrap
54 label
55 bar-coded portion
60 testing apparatus, automated
64 frame
70 sample and reagent supply
74 sample rack
78 reagent rack
79 bar-code reader
80 incubator station
84 first section
86 second section
88 motor
90 centrifuge
94 rotor
98 motor
100 analysis station
102 holding means
104 illumination assembly
106 imaging subsystem
108 processing subsystem
110 transport subsystem
112 bar code reader
115 storage rack
116 waste receptacle
122 shallow wash area
125 deep wash area
127 cell dilution packs
128 robot arm
190 drawer assembly
195 motor
196 sensor bar
197 holding area
198 barcode reader
200 test element
204 compact body
208 test chamber or column
210 top side
212 upper section
216 lower section
220 transitional section 224 wrap
230 cartridge
234 frame
238 linear array
242 end position
246 slot
280 cartridge
284 frame
300 cartridge Though only specific embodiments were described herein, it will be readily apparent that other variations and modifications are possible within the intended ambits of the present invention, according to the following claims.

The invention claimed is:

1. An apparatus for use in an immunodiagnostic test apparatus, said apparatus including:
   a storage frame;
   a plurality of test elements individually and separably retained within said storage frame, each of said test elements comprising a single reaction well containing a quantity of test material for testing a patient sample and a strip sealing said reaction well wherein said storage frame permits test elements to be separately dispensed from said frame, said storage frame including means for sequentially dispensing said test elements.

2. Apparatus as recited in claim 1, wherein said plurality of test elements are retained in said storage frame as a two-dimensional array.

3. An apparatus as recited in claim 1, further including cartridges, said cartridges each defined by an open top into which a predetermined number of said individual test elements can be dispensed from said storage frame for conduction of at least one immunodiagnostic test procedure.

4. An apparatus as recited in claim 3, wherein the predetermined number of test elements that can be dispensed into said cartridges is between 2 and 8 test elements.

5. An apparatus as recited in claim 1, wherein each said of test elements contains a quantity of inert material, including at least one of beads and gel material.

6. An apparatus as recited in claim 1, wherein each of said test elements is made from an optically transparent material.

7. An apparatus as recited in claim 1, wherein each said strip of said test elements is made from a pierceable material.

* * * * *